United States Patent
Mitchell

(10) Patent No.: US 11,116,246 B2
(45) Date of Patent: Sep. 14, 2021

(54) COMPOSITIONS OF COENZYME Q10 AND METHODS OF USE

(71) Applicant: GM Pharmaceuticals, Inc., Arlington, TX (US)

(72) Inventor: Odes W. Mitchell, Arlington, TX (US)

(73) Assignee: GM Pharmaceuticals, Inc., Fort Worth, TX (US)

(*) Notice: Subject to any disclaimer, the term of this patent is extended or adjusted under 35 U.S.C. 154(b) by 0 days.

(21) Appl. No.: 16/380,051

(22) Filed: Apr. 10, 2019

(65) Prior Publication Data

US 2019/0328022 A1 Oct. 31, 2019

Related U.S. Application Data

(60) Provisional application No. 62/662,608, filed on Apr. 25, 2018.

(51) Int. Cl.

| | | |
|---|---|---|
| *A23L 33/155* | (2016.01) | |
| *A61K 31/122* | (2006.01) | |
| *A61K 31/714* | (2006.01) | |
| *A61K 31/593* | (2006.01) | |
| *A61K 31/202* | (2006.01) | |
| *A61K 45/06* | (2006.01) | |
| *A61K 9/00* | (2006.01) | |
| *A23L 33/12* | (2016.01) | |
| *A61K 31/4415* | (2006.01) | |

(52) U.S. Cl.
CPC ............ *A23L 33/155* (2016.08); *A23L 33/12* (2016.08); *A61K 9/0053* (2013.01); *A61K 31/122* (2013.01); *A61K 31/202* (2013.01); *A61K 31/4415* (2013.01); *A61K 31/593* (2013.01); *A61K 31/714* (2013.01); *A61K 45/06* (2013.01); *A23V 2002/00* (2013.01); *A23V 2200/326* (2013.01); *A23V 2250/314* (2013.01); *A23V 2250/706* (2013.01); *A23V 2250/7052* (2013.01); *A23V 2250/7056* (2013.01); *A23V 2250/7106* (2013.01)

(58) Field of Classification Search
None
See application file for complete search history.

(56) References Cited

U.S. PATENT DOCUMENTS

| | | | | |
|---|---|---|---|---|
| 8,652,518 | B2* | 2/2014 | Finley | A61K 31/198 |
| | | | | 424/464 |
| 2007/0016779 | A1* | 1/2007 | Lyle | H04L 9/3271 |
| | | | | 713/169 |
| 2007/0116779 | A1* | 5/2007 | Mazzio | A61K 35/60 |
| | | | | 424/539 |
| 2017/0239275 | A1* | 8/2017 | Tucker | A61K 33/06 |

OTHER PUBLICATIONS

NCT01238926, Nov. 10, 2010 (Year: 2010).*

* cited by examiner

*Primary Examiner* — Craig D Ricci
(74) *Attorney, Agent, or Firm* — Winstead PC

(57) ABSTRACT

In an embodiment, a nutritional supplement including, about 0.5 mg to about 4 mg of folate, about 6.25 mg to about 50 mg of vitamin B-6, about 250 mcg to about 2000 mcg of vitamin B-12, about 75 mg to about 600 mg of coenzyme Q10 (CoQ10), about 1250 IU to about 10,000 IU of vitamin $D_3$, about 25 mg to about 200 mg of magnesium, about 25 mg to 200 mg of N-acetyl-L-cysteine, about 5 mg to about 40 mg pyrroloquinoline quinone disodium (PQQ), about 25 mg to about 200 mg of curcumin extract, about 25 mg to about 200 mg of resveratrol, about 25 mg to about 200 mg berberine, about 12.5 mcg to about 100 mcg of chromium, and about 12.5 mcg to about 100 mcg of selenium. In an additional embodiment, the aforementioned nutritional supplement in a nutritional kit that further includes an omega-3 supplement.

20 Claims, No Drawings

COMPOSITIONS OF COENZYME Q10 AND METHODS OF USE

CROSS-REFERENCE TO RELATED APPLICATIONS

This patent application claims priority from, and incorporates by reference the entire disclosure of, U.S. Provisional Patent Application No. 62/662,608 filed on Apr. 25, 2018.

TECHNICAL FIELD

The present disclosure relates generally to coenzyme Q10 and more particularly, but not by way of limitation, to compositions of coenzyme Q10 and methods of use.

BACKGROUND

This section provides background information to facilitate a better understanding of the various aspects of the disclosure. It should be understood that the statements in this section of this document are to be read in this light, and not as admissions of prior art.

Cardiovascular diseases are considered one of the top preventable diseases among most people. Genetic factors can contribute to overall heart health, but cardiovascular diseases are largely attributed to poor lifestyle habits. Among these poor lifestyle habits include poor diet, lack of regular exercise, drug and alcohol abuse, and high stress. Vitamins, minerals, and antioxidants, inter alia, are thought to be one of the most important types of supplements for protection against many forms of cardiovascular disease. Additionally, omega-3 fatty acid is thought to be an important type of supplement for protection against various forms of cardiovascular disease and to assist in promotion of overall health.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, a nutritional supplement that includes about 0.5 mg to about 4 mg of folate, about 6.25 mg to about 50 mg of vitamin B-6, about 250 mcg to about 2000 mcg of vitamin B-12, about 75 mg to about 600 mg of coenzyme Q10 (CoQ10), about 1250 IU to about 10,000 IU of vitamin $D_3$, about 25 mg to about 200 mg of magnesium, about 25 mg to about 200 mg of N-acetyl-L-cysteine, about 5 mg to about 40 mg pyrroloquinoline quinone disodium (PQQ), about 25 mg to about 200 mg of curcumin extract, about 25 mg to about 200 mg of resveratrol, about 25 mg to about 200 mg berberine, about 12.5 mcg to about 100 mcg of chromium, and about 12.5 mcg to about 100 mcg of selenium.

In an additional embodiment, a nutritional kit including a nutritional supplement that includes about 0.5 mg to about 4 mg of folate, about 6.25 mg to about 50 mg of vitamin B-6, about 250 mcg to about 2000 mcg of vitamin B-12, about 75 mg to about 600 mg of coenzyme Q10 (CoQ10), about 1250 IU to about 10,000 IU of vitamin $D_3$, about 25 mg to about 200 mg of magnesium, about 25 mg to about 200 mg of N-acetyl-L-cysteine, about 5 mg to about 40 mg pyrroloquinoline quinone disodium (PQQ), about 25 mg to about 200 mg of curcumin extract, about 25 mg to about 200 mg of resveratrol, about 25 mg to about 200 mg berberine, about 12.5 mcg to about 100 mcg of chromium, and about 12.5 mcg to about 100 mcg of selenium. The nutritional kit further includes an omega-3 supplement that includes about 625 mg to about 5000 mg fish oil concentrate, where the fish oil concentrate includes about 500 mg to about 4000 mg omega-3 fatty acid, and where the omega-3 fatty acid includes about 375 mg to about 3000 mg eicosapentaenoic acid (EPA) and about 125 mg to about 1000 mg docosahexaenoic acid (DHA).

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

In various embodiments, the present disclosure is directed to a nutritional supplement for oral administration to support overall heart health, maintain healthy blood pressure, ease symptoms brought on by statin drugs, promote healthy energy levels, decrease oxidative stress, support cell function and muscle recovery, and promote healthy blood flow. In certain embodiments, the present disclosure is directed to a nutritional supplement with heart-healthy vitamins, minerals, and antioxidants to promote heart health, soothe inflammation, and support overall cardiovascular function. In various embodiments, the nutritional supplement can be taken once daily or up to four times daily. Additional embodiments allow for higher or lower doses per day.

In addition, the nutritional supplements of the present disclosure can be combined with other supplements that can promote heart health or overall health (e.g., brain, skin, eye, and joint health). In some embodiments, the nutritional supplements of the present disclosure can be combined with an omega-3 supplement to reduce inflammation in the body, while providing other health benefits, such as, but not limited to, treating hypertriglyceridemia, helping in prevention of heart attacks or strokes, lowering blood pressure, and increasing mental health. In various embodiments, the omega-3 supplement can be taken once daily or up to four times daily. Additional embodiments allow for higher or lower doses per day. In some embodiments, the omega-3 supplement can be taken in conjunction with the nutritional supplements of the present disclosure. In some embodiments, the omega-3 supplement can be taken independently, and without use of the nutritional supplements of the present disclosure.

As both the nutritional supplement and the omega-3 supplement, disclosed in further detail herein, provide substantial health benefits, an aspect of the present disclosure relates to a nutritional kit that can include various embodiments of the nutritional supplement and the omega-3 supplement as disclosed herein. In some embodiments, the nutritional kit can be a cardio-health or heart health kit. In some embodiments, the nutritional kit can include the nutritional supplements disclosed herein with various vitamins, minerals, and antioxidants in combination with an omega-3 supplement, as discussed in further detail below. In various embodiments, the nutritional supplement and the omega-3 supplement can be taken once daily or up to four times daily, each or individually. Additional embodiments allow for higher or lower doses per day and varying dosages of each of the nutritional supplement and the omega-3 supplement.

In some embodiments, the nutritional supplement disclosed herein includes a combination of unique vitamins, minerals, and antioxidants that were specifically chosen and combined according to their biological and physiological activities. Each vitamin, mineral, and antioxidant component can be used in combination to significantly improve heart health. Described herein are advanced formulas for coenzyme Q10 (CoQ10) supplements with a combination of vitamins, minerals, and antioxidants.

CoQ10 plays a key role in the body, and most healthy people have enough CoQ10 naturally. However, there is evidence that adding more of this nutrient, in the form of CoQ10 supplements, may be beneficial for overall heart health. Increasing age and various medical conditions have been associated with dropping levels of CoQ10, and conversely, increases of CoQ10 have been used to treat many different medical conditions. There is evidence that CoQ10 supplements can lower blood pressure and increase overall heart health. CoQ10 can also be used to treat heart failure and other heart conditions by helping to improve symptoms and lessen future cardiac risks when combined with regular medications.

In addition to CoQ10, there is evidence that various minerals, vitamins, and antioxidants, can support overall heart health, maintain healthy blood pressure levels, ease symptoms brought on by statin drugs, promote healthy energy levels, decrease oxidative stress, support cell function and muscle recovery, and promote healthy blood flow. Example minerals, vitamins, and antioxidants can include, but are not limited to, folate, vitamin B-6, vitamin B-12 and vitamin $D_3$, magnesium, N-acetyl-L-cysteine (or N-acetyl cysteine), pyrroloquinoline quinone disodium (PQQ), curcumin extract, resveratrol, berberine, chromium, and selenium.

CoQ10 and PQQ can help promote healthy mitochondrial function, and when utilized together, CoQ10 and PQQ work together synergistically, and the PQQ can result in healthy mitochondria reproduction. Along with CoQ10 and PQQ, resveratrol, a number of B vitamins, magnesium, and N-acetyl-L-cysteine, all work in conjunction to help the mitochondria to work in a healthy manner. Further, it has been shown that berberine, CoQ10, and PQQ help boost depleted nutrients that are needed for a healthy heart. This can be highly advantageous to combat nutritional depletion caused by various prescription drugs.

Research indicates that a daily dose of folic acid reduces the risk of heart disease and stroke. Folic acid has been shown to effectively lower levels of homocysteine, an amino acid, in the blood. Evidence indicates that higher than normal levels of homocysteine levels are an independent risk factor for heart disease and can lead to dangerous blood clots and hardening of the arteries, and that elevated homocysteine levels increase the risk of heart disease. Thus, it has been shown that lowering homocysteine levels through the use of folic acid supplements can prevent heart disease by lower the levels of homocysteine in the body.

Moreover, studies have shown that a mild deficiency in vitamin B-6 can be associated with an increased risk of cardiovascular disease, and epidemiologic evidence has suggested that low dietary intake, or reduced blood concentrations, of vitamin B-6 is associated with an increased risk of cardiovascular disease. Vitamin B-6 and vitamin B-12, along with folic acid, have further been demonstrated to be heart-healthy due to their role in reducing homocysteine. Together, these B vitamins can affect the methylation cycle in a way that helps provide healthy homocysteine levels. In addition to the B vitamins, a growing number of studies point to vitamin D deficiency as a risk factor for heart attacks, congestive heart failure, peripheral arterial disease, strokes, and the conditions associated with cardiovascular disease, such as, high blood pressure and diabetes.

Studies indicate that vitamin $D_3$ can significantly restore the damage to the cardiovascular system caused by several diseases, including hypertension, diabetes, and atherosclerosis. Studies further indicate that a key element to heart health is endothelial function, which is a key component in maintaining vascular health. Resveratrol, along with vitamin D, are key components in healthy endothelial function.

Moreover, it has been demonstrated that endothelial senescence can contribute to the pathogenesis of age-related vascular disorders, and chronic exposure to risk factors for cardiovascular disease accelerates the effects of chronological aging by generating stress-dependent damages, including oxidative stress, thereby promoting stress-induced premature senescence. Studies have indicated that the antioxidant N-acetyl-L-cysteine delays cellular senescence in endothelial cells and thus can help control stress-induced premature senescence.

Additionally, research shows that insufficient magnesium intake increases cardiovascular risk and that magnesium is essential for the activity of the heart muscle and the nerves that initiate the heartbeat. Magnesium has also been shown to help regulate blood pressure. Adequate intake of magnesium helps prevent arrhythmias, reduce cardiac damage from oxidative stress, keep blood vessels healthy, prevent spasms of coronary arteries that can cause angina, and boost high-density lipoprotein (HDL) cholesterol levels. Observational studies have found that people with a high dietary intake of magnesium have a lower risk of heart disease and stroke.

Moreover, PQQ is a water-soluble quinone compound that has a strong anti-oxidant capacity, and studies indicate that PQQ has the ability to be a reduction-oxidation agent and is capable of circulating in the human body to combat free radicals. Studies show that this ability to transfer electrons indicates that PQQ is essential for the mitochondria to produce energy and to stimulate mitochondrial biogenesis, thus promoting overall heart health.

Studies have further suggested that curcumin may impede the development of atherosclerosis, or clogged arteries, a key risk factor for heart attacks and strokes, and that resveratrol helps prevent damage to blood vessels, reduce low-density lipoprotein (LDL) cholesterol, and prevent blood clots. Moreover, research indicates that resveratrol is linked to a lower risk of inflammation and blood clotting. Resveratrol also shows promise in improving cerebral blood flow, which is responsible for its protective effects against stroke and vascular dementia and demonstrates the ability to improve mitochondrial health, thus promoting overall heart health. Furthermore, an important factor for overall heart health includes healthy inflammatory response, which can be facilitated by the use of curcumin. Curcumin supports the body's natural ability to deal with inflammation, while berberine and resveratrol provide the ability to modulate inflammation, which in turn, promotes heart health.

Studies have indicated that berberine can regulate blood sugar levels and obesity, which in turn, can help lower risk of heart disease. Research indicates that berberine has a favorable effect on triglycerides and cholesterol levels, and has been shown to reduce apolipoprotein B, the primary apolipoprotein of chylomicrons (lipoprotein particles that contain triglycerides) and LDL particles. The addition of berberine in nutritional supplements helps keep cholesterol levels in a healthy range. Berberine can help facilitate healthy levels of LDL cholesterol, for example, by facilitating healthy ranges of LDL particle numbers and small density LDL. As such, berberine has been shown to have the ability to help maintain healthy cholesterol levels.

Furthermore, studies indicate that berberine has the ability to help regulate the expression of proprotein convertase subtilisin/kexin type 9 (PCSK9). PCSK9 binds to the receptors for LDL particles, which transport fat molecules (including cholesterol), within extracellular fluid. The LDL receptors (LDLRs) on the liver and other cell membranes bind and initiate ingestion of LDL-particles from extracellular fluid into cells, thus reducing LDL particle concentrations. When PCSK9 is blocked, more LDLRs are recycled and are present on the surface of cells to remove LDL particles from the extracellular fluid. Thus, blocking PCSK9 can lower blood LDL particle concentrations. Furthermore, research indicates the adenosine monophosphate-activated protein kinase (AMPK) activation by berberine stimulates the release of nitric oxide, a signaling molecule that relaxes the arteries, increases blood flow and lowers blood pressure, dilates blood vessels, and protects against atherosclerosis. Additionally, a major key focus on heart health is healthy blood sugar levels, and berberine has been shown to be effective at keeping blood sugar levels healthy, while chromium has been shown to be important for activating insulin receptors. It has further been demonstrated that magnesium and resveratrol help maintain healthy blood sugar levels in addition to berberine.

Research has further indicated that chromium is needed for normal metabolism of fats, including cholesterol, and further, shows a link between higher chromium intake and healthier arteries and levels of blood cholesterol. Moreover, low chromium levels have been linked to an association with raised heart attack risks. Furthermore, selenium has been shown to assist in the prevention of coronary heart disease, fight inflammation, increase blood flow, reduce free radical oxidative stress, and help with antioxidant activity. Studies further suggest that another key aspect to heart health relates to healthy thyroid function, which can be achieved with an intake of selenium, as selenium has been shown to help promote healthy thyroid function. Accordingly, chromium and selenium can be beneficial to overall heart-healthiness.

The above-mentioned studies have indicated that folate, vitamin B-6, vitamin B-12, CoQ10, vitamin $D_3$, magnesium, N-acetyl-L-cysteine, PQQ, curcumin extract, resveratrol, berberine, chromium, and selenium all promote overall heart health, maintain healthy blood pressure, ease symptoms brought on by statin drugs, promote healthy energy levels, decrease oxidative stress, support cell function and muscle recovery, and promote healthy blood flow. These studies have further indicated that the above-mentioned vitamins, minerals, and antioxidants promote heart health, soothe inflammation, and support overall cardiovascular function, and therefore promote overall health of the heart and the cardiovascular system.

As such, in various embodiments of the present disclosure, a nutritional supplement can include active ingredients, including, but not limited to, folate, vitamin B-6, vitamin B-12, CoQ10 (ubiquinone), vitamin $D_3$, magnesium, N-acetyl-L-cysteine, PQQ, curcumin extract, resveratrol, berberine, chromium, and selenium.

In certain embodiments, folate can be L-methylfolate magnesium, vitamin B-6 can be pyridoxal 5'-phosphate, vitamin B-12 can be cyanocobalamin, vitamin $D_3$ can be cholecalciferol, magnesium can be magnesium glycinate, chromium can be chromium picolinate, and selenium can be selenomethionine (L-selenomethionine).

Disclosed herein are formulas that provides optimal amounts of absorbable vitamins, minerals, and antioxidants to meet the unique nutritional requirements to promote heart health, maintain healthy blood pressure, ease symptoms brought on by statin drugs, promote healthy energy levels, decrease oxidative stress, support cell function and muscle recovery, and promote healthy blood flow. A particular example listing of active ingredients and amounts within the nutritional supplement will be described in more detail below with respect to Table 1. Amounts are given based on serving size and, as will be appreciated by those of ordinary skill in the art, "IU" refers to "international units", "mg" refers to "milligrams", and "mcg" refers to "micro grams". In typical embodiments, the daily dosage can be a single serving size as shown in Table 1 below, or up to four serving sizes per day. Additional embodiments allow for higher or lower doses per day.

In various embodiments, the nutritional supplement includes active ingredients of, for example, folate in the amount of about 1 mg, vitamin B-6 in the amount of about 12.5 mg, vitamin B-12 in the amount of about 500 mcg, coenzyme Q10 in the amount of about 150 mg, vitamin $D_3$ in the amount of about 2500 IU, magnesium in the amount of about 50 mg, N-acetyl-L-cysteine in the amount of about 50 mg, PQQ (pyrroloquinoline quinone disodium) in the amount of about 10 mg, curcumin extract in the amount of about 50 mg, resveratrol in the amount of about 50 mg, berberine in the amount of about 50 mg, chromium in the amount of about 25 mcg, and selenium in the amount of about 25 mcg.

Table 1 below illustrates a particular embodiment of a nutritional supplement of the present disclosure. In this particular embodiment, the nutritional supplement includes folate (as L-methylfolate magnesium) in the amount of about 1 mg, vitamin B-6 (as pyridoxal 5'-phosphate) in the amount of about 12.5 mg, vitamin B-12 (as cyanocobalamin) in the amount of about 500 mcg, coenzyme Q10 (ubiquinone) in the amount of about 150 mg, vitamin $D_3$ (as cholecalciferol) in the amount of about 2500 IU, magnesium (as magnesium glycinate) in the amount of about 50 mg, N-acetyl-L-cysteine in the amount of about 50 mg, PQQ (pyrroloquinoline quinone disodium) in the amount of about 10 mg, curcumin extract in the amount of about 50 mg, resveratrol in the amount of about 50 mg, berberine in the amount of about 50 mg, chromium (as chromium picolinate) in the amount of about 25 mcg, and selenium (as L-selenomethionine) in the amount of about 25 mcg.

TABLE 1

| Active Ingredient | Amount |
| --- | --- |
| Folate (as L-Methylfolate Magnesium) | 1 mg |
| Vitamin B-6 (as Pyridoxal 5'-Phosphate) | 12.5 mg |
| Vitamin B-12 (as Cyanocobalamin) | 500 mcg |
| Coenzyme Q10 (Ubiquinone) | 150 mg |
| Vitamin $D_3$ (as Cholecalciferol) | 2500 IU |
| Magnesium (as Magnesium Glycinate) | 50 mg |
| N-Acetyl-L-Cysteine | 50 mg |
| PQQ (Pyrroloquinoline Quinone Disodium) | 10 mg |
| Curcumin Extract | 50 mg |
| Resveratrol | 50 mg |
| Berberine | 50 mg |
| Chromium (as Chromium Picolinate) | 25 mcg |
| Selenium (as L Selenomethionine) | 25 mcg |

In some embodiments, the nutritional supplement includes active ingredients between about 0.5 to about 1.5 times that indicated in Table 1, for example, folate in the range of about 0.5 mg to about 1.5 mg, vitamin B-6 in the range of about 6.25 mg to about 18.75 mg, vitamin B-12 in the range of about 250 mcg to about 750 mcg, coenzyme Q10 in the range of about 75 mg to about 225 mg, vitamin $D_3$ in the range of about 1250 IU to about 3750 IU, magnesium in the range of about 25 mg to about 75 mg, N-acetyl-L-cysteine in the range of about 25 mg to about 75 mg, PQQ (pyrroloquinoline quinone disodium) in the range of about 5 mg to about 15 mg, curcumin extract in the range of about 25 mg to about 75 mg, resveratrol in the range of about 25 mg to about 75 mg, berberine in the range of about 25 mg to about 75 mg, chromium in the range of about 12.5 mcg to about 37.5 mcg, and selenium in the range of about 12.5 mcg to about 37.5 mcg.

In various embodiments, the nutritional supplement includes active ingredients between about 0.5 to about 1.5 times that indicated in Table 1, for example, folate (as L-methylfolate magnesium) in the range of about 0.5 mg to about 1.5 mg, vitamin B-6 (as pyridoxal 5'-phosphate) in the range of about 6.25 mg to about 18.75 mg, vitamin B-12 (as cyanocobalamin) in the range of about 250 mcg to about 750 mcg, coenzyme Q10 (ubiquinone) in the range of about 75 mg to about 225 mg, vitamin $D_3$ (as cholecalciferol) in the range of about 1250 IU to about 3750 IU, magnesium (as magnesium glycinate) in the range of about 25 mg to about 75 mg, N-acetyl-L-cysteine in the range of about 25 mg to about 75 mg, PQQ (pyrroloquinoline quinone disodium) in the range of about 5 mg to about 15 mg, curcumin extract in the range of about 25 mg to about 75 mg, resveratrol in the range of about 25 mg to about 75 mg, berberine in the range of about 25 mg to about 75 mg, chromium (as chromium picolinate) in the range of about 12.5 mcg to about 37.5 mcg, and selenium (as L-selenomethionine) in the range of about 12.5 mcg to about 37.5 mcg.

In certain embodiments, the nutritional supplement includes active ingredients between about 1 to about 4 times that indicated in Table 1, for example, folate in the range of about 1 mg to about 4 mg, vitamin B-6 in the range of about 12.5 mg to about 50 mg, vitamin B-12 in the range of about 500 mcg to about 2000 mcg, coenzyme Q10 in the range of about 150 mg to about 600 mg, vitamin $D_3$ in the range of about 2500 IU to about 10,000 IU, magnesium in the range of about 50 mg to about 200 mg, N-acetyl-L-cysteine in the range of about 50 mg to about 200 mg, PQQ (pyrroloquinoline quinone disodium) in the range of about 10 mg to about 40 mg, curcumin extract in the range of about 50 mg to about 200 mg, resveratrol in the range of about 50 mg to about 200 mg, berberine in the range of about 50 mg to about 200 mg, chromium in the range of about 25 mcg to about 100 mcg, and selenium in the range of about 25 mcg to about 100 mcg.

In some embodiments, the nutritional supplement includes active ingredients between about 1 to about 4 times that indicated in Table 1, for example, folate (as L-methylfolate magnesium) in the range of about 1 mg to about 4 mg, vitamin B-6 (as pyridoxal 5'-phosphate) in the range of about 12.5 mg to about 50 mg, vitamin B-12 (as cyanocobalamin) in the range of about 500 mcg to about 2000 mcg, coenzyme Q10 (ubiquinone) in the range of about 150 mg to about 600 mg, vitamin $D_3$ (as cholecalciferol) in the range of about 2500 IU to about 10,000 IU, magnesium (as magnesium glycinate) in the range of about 50 mg to about 200 mg, N-acetyl-L-cysteine in the range of about 50 mg to about 200 mg, PQQ (pyrroloquinoline quinone disodium) in the range of about 10 mg to about 40 mg, curcumin extract in the range of about 50 mg to about 200 mg, resveratrol in the range of about 50 mg to about 200 mg, berberine in the range of about 50 mg to about 200 mg, chromium (as chromium picolinate) in the range of about 25 mcg to about 100 mcg, and selenium (as L-selenomethionine) in the range of about 25 mcg to about 100 mcg.

In some embodiments, the nutritional supplement includes active ingredients between about 0.5 to about 4 times that indicated in Table 1. For example, in additional embodiments, the nutritional supplement can include about 0.5 mg to about 4 mg of folate, about 6.25 mg to about 50 mg of vitamin B-6, about 250 mcg to about 2000 mcg of vitamin B-12, about 75 mg to about 600 mg of coenzyme Q10 (CoQ10), about 1250 IU to about 10,000 IU of vitamin $D_3$, about 25 mg to about 200 mg of magnesium, about 25 mg to 200 mg of N-acetyl-L-cysteine, about 5 mg to about 40 mg pyrroloquinoline quinone disodium (PQQ), about 25 mg to about 200 mg of curcumin extract, about 25 mg to about 200 mg of resveratrol, about 25 mg to about 200 mg berberine, about 12.5 mcg to about 100 mcg of chromium, and about 12.5 mcg to about 100 mcg of selenium.

In some embodiments, the nutritional supplement can include inactive ingredients, for example, microcrystalline cellulose, croscarmellose sodium, silicon dioxide, magnesium stearate, hydroxypropyl methylcellulose, polyethylene glycol, or combinations of the same and like.

In various embodiments, the folate can be in the form of a magnesium or calcium salt. In certain embodiments, the B-6 vitamin can be in the form of pyridoxine, pyridoxine 5'-phosphate, pyridoxal, pyridoxal 5'-phosphate, pyridoxamine, pyridoxamine 5'-phosphate, 4-pyridoxic acid, or pyritinol (a semi-synthetic derivative of pyridoxine). In some embodiments, the B-12 vitamin can be in the form of cyanocobalamin, hydroxocobalamin, methylcobalamin, or adenosylcobalamin. In further embodiments, the magnesium can be in the form of chloride, glycinate, malate, sulfate, taurate and orotate, threonate, citrate, or oxide.

In certain embodiments, the chromium can be in the form of chromium picolinate, chromium chloride, chromium aspartate, chromium amino acid chelate, chromium nicotinate (polynicotinate), or glucose tolerance factor chromium (chromium GTF). In some embodiments the selenium can be organic or inorganic forms, such as selenomethionine (L-selenomethionine), selenocysteine, methylselenocysteine, or selenite.

In various embodiments, the nutritional supplement can be in the form of a pharmaceutical carry, for example, a tablet, a capsule, or the like. In some embodiments the nutritional supplement can be in liquid form, a chewable, a gummy, a tablet, a softgel, a capsule, or combinations of the same and like.

In addition, the nutritional supplements of the present disclosure can be combined with other supplements that can promote heart health or overall health (e.g., brain, skin, eye, and joint health). In some embodiments, the nutritional supplements of the present disclosure can be combined with omega-3 fatty acid supplements, and can be in the form of, for example, fish oil or alpha-linolenic acid. Fish oil is oil derived from the tissues of oily fish and include the omega-3 fatty acids eicosapentaenoic acid (EPA) and docosahexaenoic acid (DHA), precursors of certain eicosanoids that are known to reduce inflammation in the body, and have other health benefits, such as, but not limited to, treating hypertriglyceridemia, helping in prevention of heart attacks or strokes, lowering blood pressure, and increasing mental health.

Studies have shown that EPA and DHA, found in fish oil, are effective in reducing the risk of coronary heart disease, supporting the body's natural inflammatory response, supporting healthy blood flow, and maintaining healthy HDL cholesterol levels. Furthermore, studies indicate that EPA and DHA decrease blood lipids and cholesterol, and help maintain healthy triglyceride levels. Moreover, DHA assists in the reduction of neuroinflammation.

In addition to the cardiovascular benefits found in omega-3 fatty acid, studies have indicated that omega-3 fatty acid supports various other aspects of health, such as, but not limited to, eye, brain, joint, and skin health. For example, DHA is a major structural component of the eyes' retinas, and DHA intake helps prevent macular degeneration, which can cause vision impairment and blindness. Studies have shown that getting enough omega-3 is linked to a reduced risk of macular degeneration, one of the world's leading causes of permanent eye damage and blindness.

Furthermore, individuals with mental disorders often have low blood levels of omega-3 fats, and improving omega-3 fatty acid intake can improve associated symptoms. Studies suggest that omega-3 fatty acid supplements can reduce the frequency of mood swings and relapses in people with both schizophrenia and bipolar disorder. Additionally, several studies link higher omega-3 fatty acid intake to decreased age-related mental decline and a reduced risk of Alzheimer's disease. Studies have indicated that omega-3 fatty acid supplements are beneficial at disease onset, when the symptoms of Alzheimer's are very mild.

Moreover, research indicates that omega-3 fatty acid can improve bone strength by boosting the amount of calcium in the bones, which leads to a reduced risk of osteoporosis. Studies further indicate that patients taking omega-3 fatty acid supplements have reported reduced joint pain and increased grip strength, which indicate that omega-3 fatty acid assists in the treatment of arthritis.

Additionally, DHA and EPA, found in omega-3 fatty acid, show advantageous skin health properties. For example, DHA is a structural component of the skin that is responsible for the health of cell membranes which make up a large part of the skin, and a healthy cell membrane results in soft, moist, supple, and wrinkle-free skin. EPA also benefits skin in several ways, including, but not limited to, managing oil production and hydration of skin, preventing hyperkeratinization of hair follicles (appearing as little red bumps often seen on upper arms), reducing premature aging of skin, and reducing the risk of acne or acne outbreaks.

In view of the aforementioned benefits of omega-3 fatty acids, the present disclosure further relates to a nutritional supplement taken in conjunction with an omega-3 supplement. In various embodiments, the omega-3 supplement includes fish oil concentrate having omega-3 fatty acid that includes EPA and DHA.

Table 2 below illustrates a particular embodiment of an omega-3 supplement of the present disclosure. In this particular embodiment, the omega-3 supplement includes, fish oil concentrate in the amount of about 1250 mg with a total omega-3 fatty acid amount of about 1000 mg. In this particular embodiment, the about 1000 mg of omega-3 fatty acids includes about 750 mg of EPA and about 250 mg DHA. In typical embodiments, the daily dosage can be a single serving size as shown in Table 2 below, or up to four serving sizes per day. Additional embodiments allow for higher or lower doses per day.

TABLE 2

| Ingredient | Amount |
|---|---|
| Fish Oil Concentrate | 1250 mg |
| Total Omega-3 Fatty Acids | 1000 mg |
| EPA (Eicosapentaenoic Acid) | 750 mg |
| DHA (Docosahexaenoic Acid) | 250 mg |

In some embodiments, the omega-3 supplement includes ingredients between about 0.5 to about 1.5 times that indicated in Table 2, for example, fish oil concentrate in the amount of about 625 mg to about 1875 mg with a total omega-3 fatty acid amount of about 500 mg to about 1500 mg. In some embodiment, the about 500 mg to about 1500 mg of omega-3 fatty acids includes about 375 mg to about 1125 mg EPA and about 125 mg to about 375 mg DHA.

In certain embodiments, the omega-3 supplement includes ingredients between about 1 to about 4 times that indicated in Table 2, for example, fish oil concentrate in the amount of about 1250 mg to about 5000 mg with a total omega-3 fatty acid amount of about 1000 mg to about 4000 mg. In some embodiment, the about 1000 mg to about 4000 mg of omega-3 fatty acids includes about 750 mg to about 3000 mg EPA and about 250 mg to about 1000 mg DHA.

In some embodiments, the omega-3 supplement includes ingredients between about 0.5 to about 4 times that indicated in Table 2. For example, in some embodiments, the omega-3 supplement includes about 625 mg to about 5000 mg fish oil concentrate, where the fish oil concentrate includes about 500 mg to about 4000 mg omega-3 fatty acid. In some embodiment, the omega-3 fatty acid includes about 375 mg to about 3000 mg EPA and about 125 mg to about 1000 mg DHA.

In some embodiments, the omega-3 supplement can include highly concentrated omega-3, and can be in the form of, for example, fish oil or alpha-linolenic acid. In some embodiments, the fish oil can be anchovy, sardine, mackerel, or combinations of the same and like. In some embodiments, the omega-3 supplement can be in the form of capsule. In some embodiments, the capsule can be made of gelatin, glycerin, and purified water. In further embodiments, the omega-3 supplement can include natural or artificial flavors. In some embodiments, the omega-3 supplement can include natural flavors, such as, but not limited to, natural lemon flavor. In various embodiments, the omega-3 supplement can include various antioxidant agents, such as, but not limited to, tocopherols (soy), rosemary extract, ascorbyl palmitate, or combinations of the same and like.

In various embodiments, the omega-3 supplement can be in the form of a pharmaceutical carry, for example, a tablet, a capsule, or the like. In some embodiments the omega-3 supplement can be in liquid form, a chewable, a gummy, a tablet, a softgel, a capsule, or combinations of the same and like.

As both the nutritional supplement and the omega-3 supplement disclosed herein provide substantial health benefits, an aspect of the present disclosure relates to a nutritional kit that can include any embodiment of the nutritional supplement and the omega-3 supplement as disclosed herein. In some embodiments, the nutritional kit can be a cardio-health or heart health kit. In some embodiments, the nutritional kit can include the nutritional supplements disclosed herein with various vitamins, minerals, and antioxidants in combination with an omega-3 supplement as disclosed herein.

In various embodiments, the nutritional kit supports overall heart health, maintains healthy blood pressure levels, eases symptoms brought on by statin drugs, promotes healthy energy levels, decreases oxidative stress, supports cell function and muscle recovery, promotes healthy blood flow, and supports overall cardiovascular function. In some embodiments, the nutritional kit reduces risk of coronary heart disease, supports the body's natural inflammatory response, supports healthy blood flow, maintains healthy HDL cholesterol levels, decreases blood lipids and cholesterol, helps maintain healthy triglyceride levels, and reduces neuroinflammation. In some embodiments, the nutritional kit supports heart health, energy, blood flow, brain health, skin health, eye health, and joint health.

Table 3 below illustrates a particular example of a nutritional kit of the present disclosure. In this particular embodiment, the nutritional kit includes a nutritional supplement and an omega-3 supplement. In typical embodiments, the daily dosage can be a single serving size of each of the nutritional supplement and the omega-3 supplement as shown in Table 3 below, or up to four serving sizes per day. Additional embodiments allow for higher or lower doses per day.

In this particular embodiment, the nutritional supplement includes active ingredients of, such as, folate (as L-methylfolate magnesium) in the amount of about 1 mg, vitamin B-6 (as pyridoxal 5'-phosphate) in the amount of about 12.5 mg, vitamin B-12 (as cyanocobalamin) in the amount of about 500 mcg, coenzyme Q10 (ubiquinone) in the amount of about 150 mg, vitamin $D_3$ (as cholecalciferol) in the amount of about 2500 IU, magnesium (as magnesium glycinate) in the amount of about 50 mg, N-acetyl-L-cysteine in the amount of about 50 mg, PQQ (pyrroloquinoline quinone disodium) in the amount of about 10 mg, curcumin extract in the amount of about 50 mg, resveratrol in the amount of about 50 mg, berberine in the amount of about 50 mg, chromium (as chromium picolinate) in the amount of about 25 mcg, and selenium (as L-selenomethionine) in the amount of about 25 mcg. Additionally, in this particular embodiment, the omega-3 supplement includes fish oil concentrate in the amount of about 1250 mg with a total omega-3 fatty acid amount of about 1000 mg. In this particular embodiment, the about 1000 mg of omega-3 fatty acids includes about 750 mg of EPA and about 250 mg DHA.

TABLE 3

| | Amount |
|---|---|
| Nutritional Supplement | |
| Folate (as L-Methylfolate Magnesium) | 1 mg |
| Vitamin B-6 (as Pyridoxal 5'-Phosphate) | 12.5 mg |
| Vitamin B-12 (as Cyanocobalamin) | 500 mcg |
| Coenzyme Q10 (Ubiquinone) | 150 mg |
| Vitamin $D_3$ (as Cholecalciferol) | 2500 IU |
| Magnesium (as Magnesium Glycinate) | 50 mg |
| N-Acetyl-L-Cysteine | 50 mg |
| PQQ (Pyrroloquinoline Quinone Disodium) | 10 mg |
| Curcumin Extract | 50 mg |
| Resveratrol | 50 mg |
| Berberine | 50 mg |
| Chromium (as Chromium Picolinate) | 25 mcg |
| Selenium (as L Selenomethionine) | 25 mcg |
| Omega-3 Supplement | |
| Fish Oil Concentrate | 1250 mg |
| Total Omega-3 Fatty Acids | 1000 mg |
| EPA (Eicosapentaenoic Acid) | 750 mg |
| DHA (Docosahexaenoic Acid) | 250 mg |

In some embodiments, the nutritional kit can include any of the nutritional supplement and the omega-3 supplement embodiments as disclosed in further detail above. For example, in some embodiments, the nutritional supplement can include active ingredients between about 0.5 to about 1.5 times that indicated in Table 1 and the omega-3 supplement can include ingredients between about 0.5 to about 1.5 times that indicated in Table 2, as described in detail above. For example, in some embodiments, the nutritional kit can include the nutritional supplement having folate in the range of about 0.5 mg to about 1.5 mg, vitamin B-6 in the range of about 6.25 mg to about 18.75 mg, vitamin B-12 in the range of about 250 mcg to about 750 mcg, coenzyme Q10 in the range of about 75 mg to about 225 mg, vitamin $D_3$ in the range of about 1250 IU to about 3750 IU, magnesium in the range of about 25 mg to about 75 mg, N-acetyl-L-cysteine in the range of about 25 mg to about 75 mg, PQQ (pyrroloquinoline quinone disodium) in the range of about 5 mg to about 15 mg, curcumin extract in the range of about 25 mg to about 75 mg, resveratrol in the range of about 25 mg to about 75 mg, berberine in the range of about 25 mg to about 75 mg, chromium in the range of about 12.5 mcg to about 37.5 mcg, and selenium in the range of about 12.5 mcg to about 37.5 mcg. In this example embodiment, the nutritional kit can include the omega-3 supplement with fish oil concentrate in the amount of about 625 mg to about 1875 mg with a total omega-3 fatty acid amount of about 500 mg to about 1500 mg. In this example embodiment, the about 500 mg to about 1500 mg of omega-3 fatty acids includes about 375 mg to about 1125 mg EPA and about 125 mg to about 375 mg DHA.

In another example, in some embodiments, the nutritional supplement can include active ingredients between about 1 to about 4 times that indicated in Table 1 and the omega-3 supplement can include ingredients between about 1 to about 4 times that indicated in Table 2, as described in detail above. For example, in some embodiments, the nutritional kit can include the nutritional supplement having folate in the range of about 1 mg to about 4 mg, vitamin B-6 in the range of about 12.5 mg to about 50 mg, vitamin B-12 in the range of about 500 mcg to about 2000 mcg, coenzyme Q10 in the range of about 150 mg to about 600 mg, vitamin $D_3$ in the range of about 2500 IU to about 10,000 IU, magnesium in the range of about 50 mg to about 200 mg, N-acetyl-L-cysteine in the range of about 50 mg to about 200 mg, PQQ (pyrroloquinoline quinone disodium) in the range of about 10 mg to about 40 mg, curcumin extract in the range of about 50 mg to about 200 mg, resveratrol in the range of about 50 mg to about 200 mg, berberine in the range of about 50 mg to about 200 mg, chromium in the range of about 25 mcg to about 100 mcg, and selenium in the range of about 25 mcg to about 100 mcg. In this example embodiment, the nutritional kit can include the omega-3 supplement with fish oil concentrate in the amount of about 1250 mg to about 5000 mg with a total omega-3 fatty acid amount of about 1000 mg to about 4000 mg. In this example embodiment, the about 1000 mg to about 4000 mg of omega-3 fatty acids includes about 750 mg to about 3000 mg EPA and about 250 mg to about 1000 mg DHA.

In some embodiments, the nutritional supplement can include active ingredients between about 0.5 to about 4 times that indicated in Table 1 and the omega-3 supplement can include ingredients between about 0.5 to about 4 times that indicated in Table 2, as described in detail above. For example, in some embodiments, the nutritional kit can include the nutritional supplement having about 0.5 mg to about 4 mg of folate, about 6.25 mg to about 50 mg of vitamin B-6, about 250 mcg to about 2000 mcg of vitamin B-12, about 75 mg to about 600 mg of coenzyme Q10 (CoQ10), about 1250 IU to about 10,000 IU of vitamin $D_3$, about 25 mg to about 200 mg of magnesium, about 25 mg to 200 mg of N-acetyl-L-cysteine, about 5 mg to about 40 mg pyrroloquinoline quinone disodium (PQQ), about 25 mg to about 200 mg of curcumin extract, about 25 mg to about 200 mg of resveratrol, about 25 mg to about 200 mg berberine, about 12.5 mcg to about 100 mcg of chromium, and about 12.5 mcg to about 100 mcg of selenium. In this example embodiment, the nutritional kit can include the omega-3 supplement with about 625 mg to about 5000 mg fish oil concentrate, where the fish oil concentrate includes about 500 mg to about 4000 mg omega-3 fatty acid. In this example, the omega-3 fatty acid includes about 375 mg to about 3000 mg EPA and about 125 mg to about 1000 mg DHA.

In various embodiments, the nutritional supplement and the omega-3 supplement in the nutritional kit can each be in the form of a pharmaceutical carry, for example, a tablet, a capsule, or the like. In some embodiments, the nutritional supplement and the omega-3 supplement in the nutritional kit can each be in liquid form, a chewable, a gummy, a tablet, a softgel, a capsule, or combinations of the same and like.

In some embodiments, the present disclosure relates to a method of improving overall heart health. In some embodiments, the method includes taking the nutritional supplements of the present disclosure, as previously described, separately or in combination, with the omega-3 supplements of the present disclosure, as previously described. In some embodiments, the nutritional supplement can include folate, vitamin B-6, vitamin B-12, CoQ10 (ubiquinone), vitamin $D_3$, magnesium, N-acetyl-L-cysteine, PQQ, curcumin extract, resveratrol, berberine, chromium, and selenium, as described in detail above. In some embodiments, the omega-3 supplement can include fish oil concentrate having omega-3 fatty acid that includes EPA and DHA. In some embodiments, the present disclosure relates to a method of improving overall hearth health by taking nutritional supplements and omega-3 supplements from nutritional kits of the present disclosure, such as those previously described.

Although various embodiments of the methods and compositions of the present disclosure have been illustrated in the accompanying tables and described in the foregoing Specification, it will be understood that the invention is not limited to the embodiments disclosed, but is capable of numerous rearrangements, modifications, and substitutions without departing from the spirit and scope of the invention as set forth herein. It is intended that the Specification and examples be considered as illustrative only.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A nutritional supplement comprising:
   active ingredients consisting of:
   about 0.5 mg to about 4 mg of folate;
   about 6.25 mg to about 50 mg of vitamin B-6;
   about 250 mcg to about 2000 mcg of vitamin B-12;
   about 75 mg to about 600 mg of coenzyme Q10 (CoQ10);
   about 1250 IU to about 10,000 IU of vitamin $D_3$;
   about 25 mg to about 200 mg of magnesium;
   about 25 mg to about 200 mg of N-acetyl-L-cysteine;
   about 5 mg to about 40 mg pyrroloquinoline quinone disodium (PQQ);
   about 25 mg to about 200 mg of curcumin extract;
   about 25 mg to about 200 mg of resveratrol;
   about 25 mg to about 200 mg berberine;
   about 12.5 mcg to about 100 mcg of chromium; and
   about 12.5 mcg to about 100 mcg of selenium; and
   one or more inactive ingredients selected from the group consisting of microcrystalline cellulose, croscarmellose sodium, silicon dioxide, magnesium stearate, hydroxypropyl methylcellulose, and polyethylene glycol.

2. The nutritional supplement of claim 1, wherein the folate is about 1 mg.

3. The nutritional supplement of claim 1, wherein the vitamin B-6 is about 12.5 mg.

4. The nutritional supplement of claim 1, wherein the vitamin B-12 is about 500 mcg.

5. The nutritional supplement of claim 1, wherein the CoQ10 is in about 150 mg.

6. The nutritional supplement of claim 1, wherein the vitamin $D_3$ is about 2500 IU.

7. The nutritional supplement of claim 1, wherein the magnesium is about 50 mg.

8. The nutritional supplement of claim 1, wherein the NAC is about 50 mg.

9. The nutritional supplement of claim 1, wherein the PQQ is about 10 mg.

10. The nutritional supplement of claim 1, wherein the chromium is about 25 mcg.

11. The nutritional supplement of claim 1, wherein the selenium is about 25 mcg.

12. The nutritional supplement of claim 1, wherein the folate is a magnesium salt or a calcium salt.

13. A nutritional kit comprising:
    a nutritional supplement comprising active ingredients consisting of:
    about 0.5 mg to about 4 mg of folate;
    about 6.25 mg to about 50 mg of vitamin B-6;
    about 250 mcg to about 2000 mcg of vitamin B-12;
    about 75 mg to about 600 mg of coenzyme Q10 (CoQ10);
    about 1250 IU to about 10,000 IU of vitamin D3;
    about 25 mg to about 200 mg of magnesium;
    about 25 mg to about 200 mg of N-acetyl-L-cysteine;
    about 5 mg to about 40 mg pyrroloquinoline quinone disodium (PQQ);
    about 25 mg to about 200 mg of curcumin extract;
    about 25 mg to about 200 mg of resveratrol;

about 25 mg to about 200 mg berberine;
about 12.5 mcg to about 100 mcg of chromium; and
about 12.5 mcg to about 100 mcg of selenium; and
one or more inactive ingredients selected from the group consisting of microcrystalline cellulose, croscarmellose sodium, silicon dioxide, magnesium stearate, hydroxypropyl methylcellulose, and polyethylene glycol; and an omega-3 supplement comprising about 625 mg to about 5000 mg fish oil concentrate, wherein the fish oil concentrate comprises about 500 mg to about 4000 mg omega-3 fatty acid, and wherein the omega-3 fatty acid comprises about 375 mg to about 3000 mg eicosapentaenoic acid (EPA) and about 125 mg to about 1000 mg docosahexaenoic acid (DHA).

14. The nutritional kit of claim 13, wherein the fish oil concentrate is about 1250 mg.

15. The nutritional kit of claim 13, wherein the omega-3 fatty acid is about 1000 mg.

16. The nutritional kit of claim 13, wherein the EPA is about 750 mg.

17. The nutritional kit of claim 13, wherein the DHA is about 250 mg.

18. The nutritional supplement of claim 1, wherein the curcumin extract is about 50 mg.

19. The nutritional supplement of claim 1, wherein the resveratrol is about 50 mg.

20. The nutritional supplement of claim 1, wherein the berberine is about 50 mg.

\* \* \* \* \*